United States Patent [19]

Tutt et al.

[11] Patent Number: 5,252,256
[45] Date of Patent: Oct. 12, 1993

[54] PASSIVE PROTECTION OF OPTICALLY SENSITIVE MATERIALS WITH TRANSITION METAL ORGANOMETALLIC CLUSTER COMPOUNDS

[75] Inventors: Lee W. Tutt, Thousand Oaks; Stephen W. McCahon, Newbury Park, both of Calif.

[73] Assignee: Hughes Aircraft Company, Los Angeles, Calif.

[21] Appl. No.: 502,076

[22] Filed: Mar. 29, 1990

[51] Int. Cl.$^5$ .......................... F21V 9/00; G02B 5/24
[52] U.S. Cl. .................................. 252/582; 359/885
[58] Field of Search ............... 252/582, 584, 587, 588, 252/589; 359/885

[56] References Cited

U.S. PATENT DOCUMENTS

| | | | |
|---|---|---|---|
| 3,620,597 | 11/1971 | Schwartz et al. | 359/885 |
| 4,657,345 | 4/1987 | Gordon | 252/582 |
| 4,723,248 | 2/1988 | Harter et al. | 372/25 |
| 4,885,114 | 12/1989 | Gordon et al. | 252/587 |
| 4,890,075 | 12/1989 | Pohlmann | 330/4.3 |
| 5,026,885 | 6/1991 | Bell et al. | 556/47 |
| 5,080,469 | 1/1992 | McCahon et al. | 359/241 |

FOREIGN PATENT DOCUMENTS 99524 2/1984 European Pat. Off.
292176 11/1988 European Pat. Off.

OTHER PUBLICATIONS

A. J. White et al., Journal of Chemical Education, vol. 57, No. 4, (1980), pp. 317-319.

Psaro et al., "The Thermal Behaviour of Some Polynuclear Neutral Cyclopentadienyl Carbonyl Complexes of Ni, Fe, and Ru: A thermogravimetric and Infrared Investigation", *J. of Molecular Catalysis*, vol. 16, (1982), pp. 117-129.

King, R. B., "Organometallic Chemistry of the Transition Metals. XVI.Polynuclear Cyclopentadienylmetal Carbonyls of Iron and Cobalt", Inorganic Chemistry, vol. 15, No. 12, Dec. 1966, pp. 2227-2230.

White and Cunningham, "Synthesis and Electrochemistry of Cyclopentadienylcarbonyl iron Tetramer", *J. Chemical Education, vol. 57, No. 4, 1980, pp. 317-319*.

Geoffroy and Wrighton, "Organometallic Photochemistry", Academic Press, 1979, pp. 12-15 and 143-148.

Purcell and Kotz, "Inorganic Chemistry" W. B. Saunders Company, 1977, pp. 793-803 and 1036-1039.

Blackmore, T. et al., "Chemistry of the Metal Carbonyls, Part LIII, Some Dicarbonyl-(pi-cyclopentadienyl) Ruthenuim Complexes Containing Metal-Metal Bonds" *J. Chem. Soc.(A)* (1968) pp. 2931-2936.

L. W. Tutt et al., "Optical Limiting Via Reverse Saturable Absorption in Metal Cluster Compounds", *Conference on Laser and Electro-Optics 1989 Technical Digest Series*, vol. 11, Apr. 24, 1989, Washington, pp. 158-160.

R. C. Hoffman et al., "Reverse Saturable Absorbers: Indanthrone and its Derivatives" *J. of the Optical Society of America*-B vol. 6, No. 4, Apr. 1989, New York, pp. 772-777 and Abstract.

(List continued on next page.)

Primary Examiner—Robert L. Stoll
Assistant Examiner—Philip Tucker
Attorney, Agent, or Firm—V. D. Duraiswamy; W. K. Denson-Low

[57] ABSTRACT

Optically sensitive materials such as sensors or the human eye are passively protected against overexposure to high intensity light in the visible range using a reverse saturable absorber organometallic cluster compound having a core of at least two multiply-bonded transition metal atoms selected from group 8, 6b, or 7b of the periodic table. The core atoms are bound together with ligands that permit the formation of a complex. A preferred organometallic cluster compound is cyclopentadienyl iron carbonyl tetramer. As the intensity of incident light increases, the intensity of transmitted light also increases up to a saturation level, but above the saturation level the transmitted light intensity remains substantially constant even with increasing incident light.

1 Claim, 3 Drawing Sheets

OTHER PUBLICATIONS

L. W. Tutt, "Reverse Saturable Absorption in Metal Cluster Compounds", *Optics Letters*, vol. 15, No. 12, Jun. 15, 1990, New York, pp. 700–702.

Applied Optics (Swope and Koester) May 1965 pp. 523–526 vol. 4, No. 5 "Eye Protection Against Lasers".

Hagan et al., "Passive Broadband High Dynamic Range Semi-Conductor Limiters", SPIE vol. 1105, Materials for Optical Switches, Isolators, and Limiters (1989), pp. 103–113.

Tutt et al., "Optical Limiting Via Reverse Saturable Absorption in Metal Cluster Compounds", CLEO '89/Wednesday Morning, pp. 158–160.

K. P. J. Reddy, "An Analysis of Pulse Propagation Through a Saturable Absorber Having Excited-State Absorption", Optical and Quantum Electronics 19 (1987), pp. 203–208.

"Optical Limiting in Solutions of Metallo-phthalocyanines and Naphthalocyanines", D. R. Coulter, et al., SPIE vol. 1105, Materials for Optical Switches, Isolators, and Limiters (1989), pp. 42–51.

PASSIVE PROTECTION OF OPTICALLY SENSITIVE MATERIALS WITH TRANSITION METAL ORGANOMETALLIC CLUSTER COMPOUNDS

GOVERNMENT RIGHTS

This invention was made with Government support under Contract No. N62269-87-C-0263 awarded by the Department of the Navy. The Government has certain rights in this invention.

BACKGROUND OF THE INVENTION

The present invention relates to light-absorbing materials, and, more particularly, to materials that passively protect optically sensitive materials from overexposure to high intensity light.

Optically sensitive materials such as optical sensors and the human eye are used to detect light because they contain components which are sensitive to light energy, and produce measurable reactions when exposed to light energy. In one common example, an optoelectronic sensor such as an "electric eye" produces a voltage when light falls upon a sensing material within the sensor. However, such sensors can be "blinded" by overexposure to high intensity light, just as the human eye becomes blinded if it is exposed to overly intense light. In each case, exposure to a high intensity of light can temporarily or even permanently destroy the ability of the optically sensitive material to react to light.

Many situations of potential damage to the human eye are well known. A welder uses a dark shield when the welding arc is lit, and removes the shield to inspect the job after the arc ceases. Persons working with lasers must be very careful not to expose their eyes to the direct energy of the laser beam. Optical sensors that in some senses mimic the behavior of the human eye require similar consideration. If a sensor that is monitoring a welding operation is suddenly exposed to the direct arc light without any protection, it may be damaged. Laser monitoring devices may be damaged if suddenly exposed to the full intensity of the laser beam, without proper protection.

There are two approaches to protecting such optically sensitive materials against blinding by overexposure to high intensity light. In an "active" approach, when the electronic circuitry of the optically sensitive device detects a harmfully high intensity of light, it operates a mechanism to interpose a physical barrier between the light source and the optically sensitive material. For an optoelectronic sensor, the barrier could be a solid shutter that is placed between the light source and the sensor. For the human eye, the eyelid is closed when the light intensity becomes too high. Active protection systems work well when the onset of high intensity light is fairly slow so that the protection system has time to respond, or when the interposition of the protective barrier does not pose an inconvenience. When a welder places a dark glass before his eyes as he strikes the welding arc and removes it when he finishes the weld and needs to inspect it, he is using an active protection system.

On the other hand, in some instances the onset of the harmful high-intensity light is so fast that no active system has the time to respond, and in that case a "passive" protection approach is needed. In a passive protection system, a barrier is formed directly in response to the incidence light, without the need for the operation of any device or mechanism having a delay time for response. Passive protection systems therefore do not lose effectiveness because of disablement of a mechanism, and are more convenient to use in some situations. For example, a more convenient and safer approach for the protection of a welder's eye would be a passive system such as a goggle that turns dark when the arc is struck and lightens when the arc is turned off.

An example of an existing passive protection device is photochromic sunglasses whose light absorption increases in bright light and decreases in light of lower intensity. While this type of device works well in some circumstances, it is not satisfactory in others. Photochromic transitions tend to be rather slow, typically on the order of seconds, as they depend upon the occurrence of chemical reactions within the protective material. A photochromic protective shield would not be effective as a protective barrier against an intermittently pulsed laser or for many welding situations, because the damaging intensity of light is reached within milliseconds after the initiation of the light. Thus, persons working around lasers emitting light in the visible range would not have their eyes properly protected by photochromic sunglasses, because the laser pulses would rise to the harmful range too rapidly for the sunglasses to respond. A welder would similarly be unprotected against at least the initial portions of the arc.

One potential solution to the need for better passive protective devices is found in reverse saturable absorbing (RSA) materials. When interposed in a light beam, such materials permit a fraction of incident light to pass up to some limiting value, and then limit the amount of transmitted light above that value. The functioning of RSA materials depends upon electronic transitions rather than chemical reactions, and therefore protection can be achieved in far less than a millisecond after initiation of the harmful light.

RSA materials such as Indanthrone, Sudanschwarz B, metal dithizonates, chloroaluminum phthalocyanine, and spiropyrans have been known for some time. While operable in a laboratory environment, these materials have drawbacks that limit their utilization in many practical applications. Some of the materials have a limiting transmission that is so high that the sensor may be damaged at that level. Some materials have absorption bands that limit their usefulness over a full spectrum of incident light. Others become chemically unstable even at only slightly elevated temperatures. Others cannot be processed in any reasonable fashion because they are not soluble in common solvents. Many of the candidate RSA materials suffer from more than one of these problems. As a result of these various shortcomings, to date there have been no practical applications of reverse saturable absorber materials in situations requiring protection of the eye or of other types of optical sensors.

There is a need for an improved passive protection approach and reverse saturable absorber material that is operable over a broad spectrum of visible light, is stable, and can be processed. The present invention fulfills this need, and further provides related advantages.

SUMMARY OF THE INVENTION

The present invention provides an apparatus and method for passively protecting light sensitive materials from the adverse effects of overexposure to high intensity light. The light sensitive materials are typically found in optical sensors such as optoelectronic sensors or the human eye, and the present approach permits the sensor to continue to operate and view its target while simultaneously protecting it from the harmful effects of the high intensity light. The apparatus and method of the invention are operable over the broad spectrum of visible light, thereby differing from those specialized filters that remove light over a narrow band. The protective materials are stable to moderately elevated temperatures and are also readily processed to usable form.

In accordance with the invention, a method for protecting a light sensitive material from high-intensity light comprises the step of placing over the optically sensitive material an absorber medium including a reverse saturable absorber formed of an organometallic cluster compound including at least two multiply-bonded transition metal atoms.

The organometallic cluster compound exhibits reverse saturable absorber (RSA) behavior over a broad range of the visible spectrum. As the intensity of visible light increases below an incident intensity limiting value, the intensity of transmitted light also increases. However, once the intensity of the incident light reaches the incident intensity limiting value, the organometallic cluster compound absorbs all excess light intensity, so that the transmitted intensity saturates at a saturation value. The cluster compound may be carried in a carrier material such as a solvent, a polymer, a sol gel glass, or a porous glass so as to dilute the cluster compound, permitting the saturation value to be adjusted through dilution of the RSA material in the absorber. The transmitted intensity at incident light intensities greater than the limiting value may thereby be adjusted to the requirements of particular light sensitive materials and devices that are being protected.

The organometallic cluster compound includes a core of at least two multiply-bonded transition metal atoms from group 8, group 6b, or group 7b of the periodic table. The core is held together so that an organometallic complex is formed by the binding effect of ligands attached to the metal atoms. A variety of ligands can be used, as long as they permit the formation of a stable complex. In the preferred approach, the ligands are selected according to the "18 electron rule" well known in the field of organometallic complex chemistry.

Light absorption is by an electronic transition mechanism operable in all of the group 6b, 7b, and 8 transition metals. The required electronic transitions occur in subnanosecond times, so that the passive protection effect is operable to shield light sensitive materials from light pulses or beams whose rise times are very short. Since the rise time of pulses of many types of pulsed lasers is on the order of 10 nanoseconds or less, optical protectors using the shielding materials of the invention provide excellent protection against overexposure by pulsed lasers. The materials of the invention also protect against damage by longer pulses in the microsecond to millisecond range, and even for continuous pulses, although for such longer duration pulses active protection mechanisms may be preferable.

The present invention therefore provides an important advance in the art of passive optical protection systems for shielding against the adverse effects of overexposure to high intensities of visible light. Other features and advantages of the present invention will be apparent from the following more detailed description of the preferred embodiment, taken in conjunction with the accompanying drawing, which illustrates, by way of example, the principles of the invention.

DETAILED DESCRIPTION OF THE INVENTION

In accordance with the invention, a passive optical protector comprises a shield formed of a semi-transparent absorber medium including a reverse saturable absorber formed of an organometallic cluster compound comprising a core of at least two multiply-bonded transition metal atoms selected from group 8, 6b, or 7b of the periodic table bonded together with ligands that permit the formation of a complex.

Further in accordance with the preferred approach, a method for protecting a light sensitive material from light of high intensity while permitting it to receive light of low intensity comprises the step of placing between a light source and an optically sensitive material a semi-transparent absorber medium including a reverse saturable absorber formed of an organometallic cluster compound comprising a core of at least two multiply-bonded transition metal atoms selected from group 8, 6b, or 7b of the periodic table bonded together with ligands that permit the formation of a complex.

Figure 1:
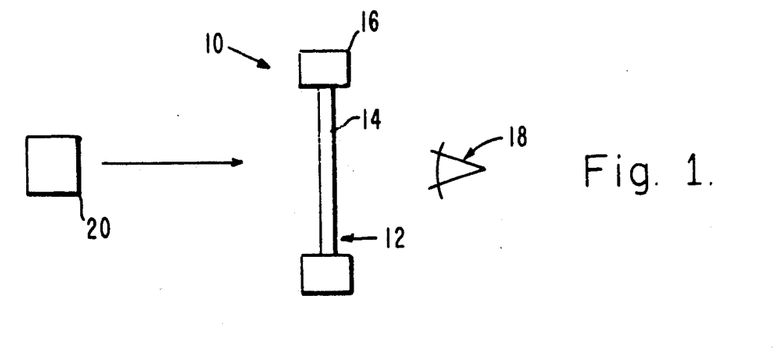
FIG. 1 is a schematic illustration of a passive laser protection apparatus.

FIG. 1 illustrates one form of a passive optical protection apparatus 10. The apparatus 10 includes a shield 12 of an absorber medium 14 mounted in a frame 16. The absorber medium 14 includes a reverse saturable absorber material made of an organometallic cluster compound, as will be described in greater detail subsequently. The protective apparatus 10 is positioned to protect a sensor 18 made of a light sensitive material. The sensor 18 may be, for example, an optoelectronic device or the human eye. The light sensitive material, which in the case of an optoelectronic device may be a photoelectronic material such as doped silicon, germanium, or gallium arsenide, produces an electrical current dependent upon the intensity of the light striking it. If the intensity for the light exceeds a safe operating intensity for the light sensitive material, it may be temporarily or permanently damaged and placed out of commission.

The protective apparatus 10 is placed in a line of sight between the sensor 18 and a light source 20 at which the sensor 18 is directed. In normal operation, the sensor 18 monitors the intensity of light produced by the light source 20. There is the possibility that, on an occasional basis, the intensity of light from the light source 20 increases greatly, such that in the absence of protection the intensity of light would be so great as to damage the sensor 18. The protective apparatus 10 prevents that damage by limiting the intensity of light that reaches the sensor 18.

Figure 2:
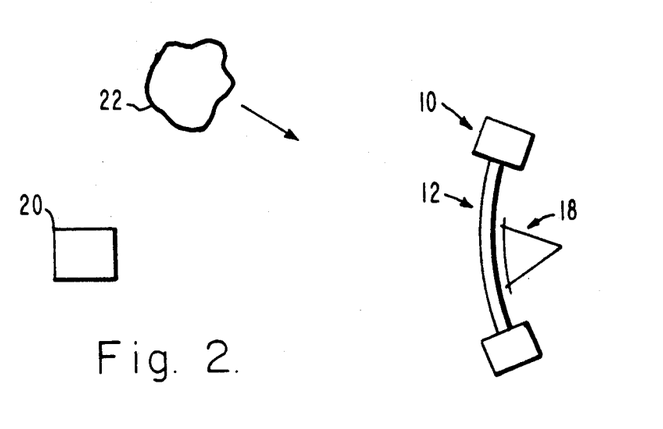
FIG. 2 is a schematic illustration of another configuration of laser protection apparatus.

FIG. 2 illustrates another application for the protective apparatus 10. Here, the elements are similar except that the increased intensity of light comes from a second source 22. That is, the sensor 18 continuously views the light source 20, which produces a light intensity that varies within the safe range of sensor operation. The second source 22 occasionally operates to produce a pulse of light that may blind the sensor 18. In this instance the protective apparatus 10 is placed over the sensor 18 in the manner of a goggle so that it intercepts the light from both sources 20 and 22, rather than just in a line of sight between the source being viewed 20 and the sensor 18. The burst of light from the second source 20 will cause the passive protective apparatus 10 to operate.

Figure 3:
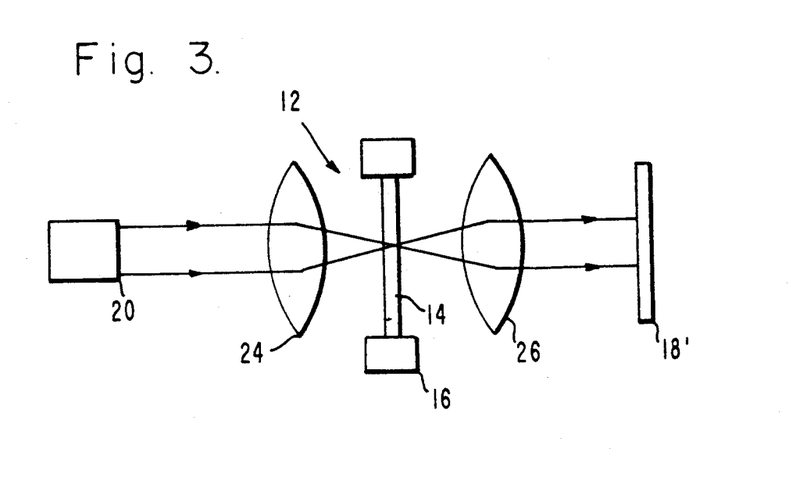
FIG. 3 is a schematic illustration of yet another configuration of laser protection apparatus.

Yet another embodiment of the protective apparatus 10 is illustrated in FIG. 3. The elements are similar to those of FIG. 1, with light produced by a source 20 and being received by a sensor 18', here shown as a flat-plate optoelectronic sensor. The light from the source 20 passes through a first lens 24 that converges the beam through a focal point to a second lens 26 that directs the beam to the sensor 18'. The shield 12 is preferably placed between the two lenses 24 and 26, most preferably near the focal point. The absorber medium 14 of the shield 12 limits the intensity of focused light. As a result, after divergence back to a defocused beam the maximum intensity of the beam is reduced by a ratio of about the size of the beam at focus to the size of the beam at the defocused state. For example, in one apparatus 10 as depicted in FIG. 3, the shield 12 was prepared with a saturation transmitted intensity of about 200 millijoule per square centimeter. The ratio of the beam diameter at the location of the shield 12 to the beam diameter at the sensor 18 was about $10^{-5}$, so that the limiting intensity of the beam of light reaching the sensor 18 was about 2 microjoule per square centimeter.

The present approach to the utilization of the protective apparatus and materials of the invention is not limited to these preferred embodiments, which are illustrative.

Figure 4:
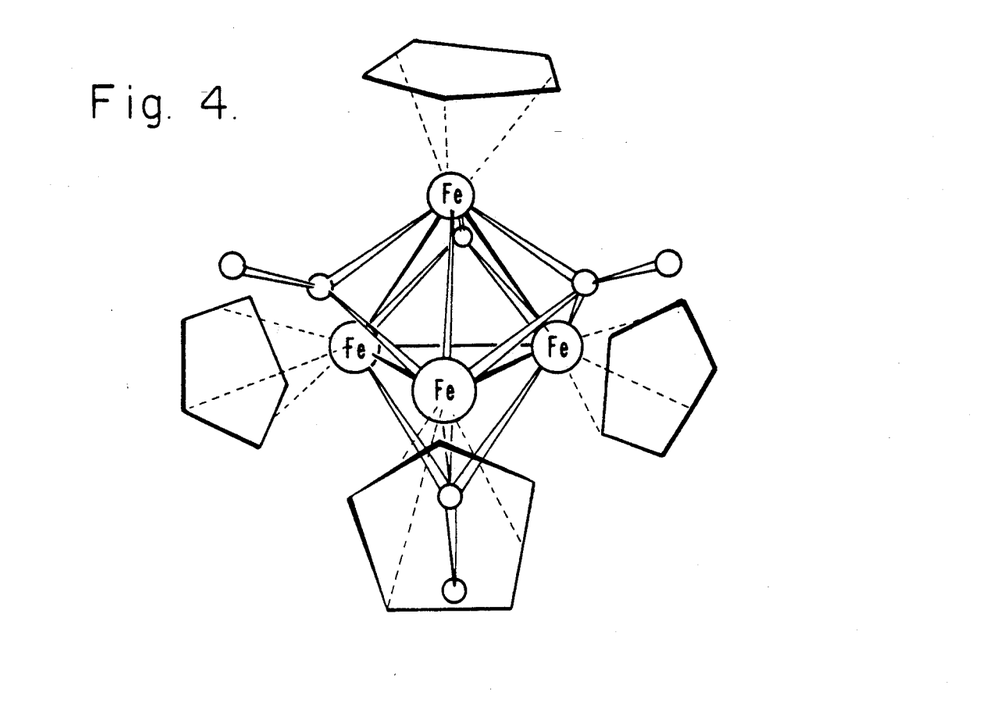
FIG. 4 is a diagrammatic view of the structure of cyclopentadienyl iron carbonyl tetramer.

The preferred RSA organometallic cluster compound for use in the absorber medium 14 is cyclopentadienyl iron carbonyl tetramer, whose structure is depicted in FIG. 4. Four iron atoms are arranged in a tetrahedron to form the core of the compound. Four carbonyl (CO) groups are associated with the tetrahedron. Four cyclopentadienyl groups are arranged at the corners of the tetrahedron, and interact by bonding together to form a stable complex. The cyclopentadienyl iron carbonyl tetramer is stable upon heating to temperatures up to about 200° C. (see Psaro et al., "The Thermal Behaviour of Some Polynuclear Neutral Cyclopentadienyl Carbonyl Complexes of Ni, Fe, and Ru: A thermogravimetric and Infrared Investigation", *J. of Molecular Catalysis*, vol. 16 (1982), pages 117–129, at page 123). The organometallic tetramer is soluble at ambient temperature in conventional solvents such as methylene chloride, acetone, ether, chloroform, and tetrahydrofuran. The organometallic tetramer may also be operably carried in a mixture with polymerizable monomers, and then solidified into place to form a solid material upon polymerization to form the polymer. For example, the organometallic tetramer has been formed as a solid within poly(methylmethacrylate) polymer.

The cyclopentadienyl iron carbonyl tetramer is a known compound described in various publications such as R.B. King, "Organometallic Chemistry of the Transition Metals. XVI. Polynuclear Cyclopentadienylmetal Carbonyls of Iron and Cobalt", *Inorganic Chemistry*, Vol. 5, No. 12, December 1966, pages 2227–2230, which also describes one method of preparation at page 2227. The organometallic tetramer has been studied and used for various applications such as an electrochemical standard, but its reverse saturation absorption properties have not heretofore been known.

The procedure generally set forth by King has been used to prepare the cyclopentadienyl iron carbonyl tetramer. Fifty grams of the commercially available compound iron dicarbonyl cyclopentadienyl, [Fe(CO)$_2$Cp]$_2$ (where Cp is an abbreviation for cyclopentadienyl), was dissolved into 500 milliliters of a solution of xylene containing a small amount of sodium and benzophenone to getter water that might otherwise be present. The black solution was refluxed for 7 days under a nitrogen atmosphere. The black precipitate was filtered and extracted with toluene. The filtrate was placed into a refrigerator at 3° C. to precipitate black crystals that were filtered and recrystallized to yield about 250 milligrams of an air-stable, dark green final product.

Another approach for preparing the cyclopentadienyl iron carbonyl tetramer that is expected to provide higher yields in shorter times is set forth in White and Cunningham, "Synthesis and Electrochemistry of Cyclopentadienylcarbonyliron Tetramer", *J. Chemical Education*, vol. 57, no. 4 (1980) at pages 317–319.

To prepare a solution of about $10^{-4}$ molar concentration of the organometallic tetramer in a solvent, about 50 parts per million by weight of cyclopentadienyl iron carbonyl tetramer was stirred into and dissolved in methylene chloride.

To prepare a solid polymerized structure containing the organometallic tetramer, two different approaches have been utilized. In the first, the tetramer was found to be directly soluble in methyl methacrylate. Cyclopentadienyl iron carbonyl tetremer was dissolved into methyl methacrylate to a concentration of about $10^{-4}$ molar. A benzoyl peroxide catalyst was added and the mixture heated to 50° C. for 4 hours to polymerize the methyl methacrylate to form poly(methylmethacrylate). In a second test, a $10^{-3}$ molar solution was formed in the same manner, and polymerized at a temperature of 70° C. for 24 hours.

In a second approach to preparing a polymerized structure containing the tetramer, cyclopentadienyl iron carbonyl tetramer in a concentration of about $10^{-4}$ molar and previously polymerized poly(methylmethacrylate) were dissolved into methylene chloride. The methylene chloride solvent was slowly evaporated at ambient temperature for 24 hours, to form a transparent solid piece having a thickness of about 1 millimeter. No bubbles were observed in the solid material. Using the same technique, transparent solid pieces of thickness ½ and 2 millimeters were prepared, again without any bubbles that might impair optical performance.

Shields containing a concentration of the absorber compound can be prepared with very small concentrations of the RSA material to as high as 10 percent, or even higher if necessary. This easy preparation of commercially valuable shields and other pieces is an important advantage of the present materials.

A solid absorber medium can therefore be prepared either by polymerization of a solution containing a monomer mixture and the tetramer, or by solidifying a mixture of a previously polymerized polymer and the tetramer. Additionally, sol gel glass or porous glass can be used as a carrier for the transition metal cluster compound.

If the organometallic tetramer is provided in a liquid solution, the frame 16 that holds the absorber medium 14 will necessarily include at least transparent glass face sheets to hold the liquid in place. If the organometallic tetramer is provided in the form of a solid as its pure form or in the described polymerized structure, then the frame 16 simply holds that solid in place as the absorber medium.

The fraction of the organometallic tetramer in solution or in the solid body and the thickness of the absorber medium, together with the saturation value of the transmitted light, determine the absorption of light by the absorber medium 14. The saturation value of the transmitted light is about 0.2 Joules per square centimeter, for a 60 percent transmitting sample. For a typical silicon sensor, the allowable light intensity within the safe range is about 0.5 joules per square centimeter. Protection using the apparatus 10 is therefore achieved with a 1 millimeter thick shield 12 of the preferred organometallic tetramer in poly (methyl methacrylate), prepared as previously described and using an apparatus like that of FIG. 3. The actual shield thickness to achieve particular protective levels will depend upon the maximum intensity that can be sustained by the optical sensor, the specific RSA material used, and its concentration, so that the preceding calculation is intended to be illustrative of the approach taken.

Other organometallic cluster compounds having a core of two or more transition metals are equally operable, as may be understood from a consideration of the electron transition states of this class of compounds. This group 8 class of transition metals includes iron, ruthenium, osmium, cobalt, rhodium, iridium, nickel, palladium, platinum, and, for the purposes of the present invention, mixtures of these elements. These elements and mixtures are characterized by their nearly full, but unfilled, d-electron shells, which gives rise to the similar reverse saturable absorber behavior.

Figure 5:
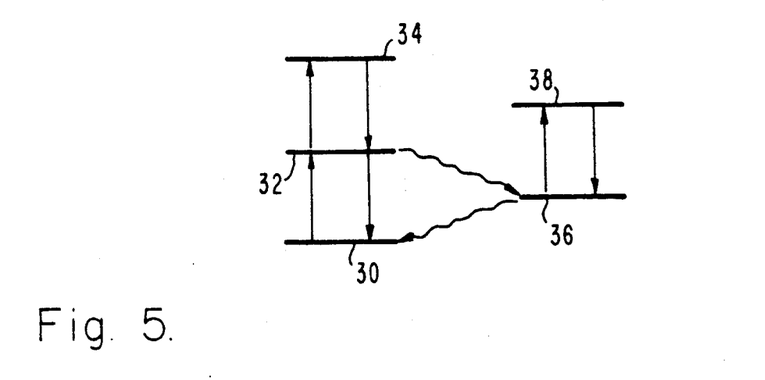
FIG. 5 is an electronic state transition diagram for an organometallic cluster compound formed from multiply-bonded transition metals.

FIG. 5 illustrates the pertinent electron transitions that occur in group 8 transition metals, and that in turn produce the reverse saturable absorber behavior. d-shell electrons exist in a singlet ground state 30, but can be excited to a first singlet excited state 32. Those electrons in the state 32 can then either be excited to a second singlet excited state 34, or can transfer to a slightly lower level of a first triplet state 36 by intersystem crossing. Electrons in the first triplet state 36 can be excited to a second triplet state by the incident energy. The general features of electron transitions in these materials are set forth in Geoffroy and Wrighton, "Organometallic Photochemistry", Academic Press, 1979, at pages 12-15 and 143-148.

For reverse saturable absorption to occur, the transition to the second singlet excited state 34 and the first triplet state 36 must have larger absorption cross sections than do the ground state 30 transitions to the first excited state 32, and the first triplet state 36 should have a relatively long lifetime (for decay to the ground state 30) compared to the intersystem crossing time and the excitation time to the second triplet state 38 and the duration of the incident energy pulse, to permit significant populations to develop in the first triplet state 36. This type of behavior is found in the group 8 transition metals and mixtures of the group 8 transition metals. The RSA behavior observed for the preferred cyclopentadienyl iron carbonyl tetramer is thus observed for other transition metal cluster compounds, as will be discussed subsequently. In fact, the group 8 atoms in the fifth and sixth periods have much higher spin orbit coupling between the first singlet excited state and the first triplet state than do group 8 atoms in the fourth period. The result is a higher intersystem crossing rate from a singlet to a triplet state, due to easing of the formal selection rules for transitions. This allows a faster and greater population of the triplet state and therefore lowers the activation threshold, leading to better RSA performance.

As the incident light falling upon the absorbing medium increases, the population of the first triplet state 36 increases, so that the triplet state excitation becomes the dominant absorbing level. With ever increasing incident light intensity above a threshold level, the transition from the first to the second triplet states absorbs the incident intensity so that the RSA saturation characteristic is observed.

The group 6b transition metals (chromium, molybdenum, and tungsten, and mixtures thereof), and the group 7b transition metals (manganese, technetium, and rhenium, and mixtures thereof) exhibit the same type of behavior. They are therefore acceptable for use in the core of the transition metal complex compound, although the group 8 transition metals remain preferred.

The core is formed of at least two, and typically more, transition metal atoms, as long as the atoms are multiply bonded. That is, each transition metal atom must be bonded to at least two other atoms, so that if one bond is broken the atom is not lost to the core. A desirably stable tetrahedrally configured and bonded core is formed from four transition metal atoms, but larger or smaller numbers of transition metal atoms may form the core. In the case of two atoms forming the core, there must be two bonds between the two atoms, so if one bond is broken the core will not disintegrate.

Within these constraints, the core may be formed of two or more multiply-bonded transition metal (group 8, 6b, or 7b) atoms, of the same or different types. The preferred cyclopentadienyl iron carbonyl tetramer discussed previously has four atoms of the same type, iron. Other cluster compounds may have different types of transition metal atoms in the core, such as the iron tricobalt complex compounds to be discussed subsequently.

The ligand chosen for incorporation into the cluster compound serves two functions. First, it effects the binding to hold the core of transition metal core atoms together as a complex. Second, it enters into the electron transition behavior in a secondary fashion that can be used to tailor the complex compound light absorption characteristics. The electron transition from the first or ground triplet state 36 to the second or excited triplet state 38 is through metal-to-ligand or ligand-to-metal charge transfers, which interact strongly with light. Changing the ligand can influence the light-absorption cross section, thereby altering the absorption properties and the saturation value of the compound.

To effect binding, the ligand is chosen so that the compound satisfies the well-known "18 electron" rule, which has been described in detail in Purcell and Kotz, "Inorganic Chemistry", W. B. Saunders Company, 1977, at pages 793-803 and 1036-1039; and Geoffroy and Wrighton, "Organometallic Photochemistry", Academic Press, 1979, at pages 8-9. That is, the ligand must supply a sufficient number of electrons such that the shells of the core metal atoms are filled. Thus, for example, in the case of the preferred cyclopentadienyl iron carbonyl tetramer, each cyclopentadienyl ligand supplies 5 electrons, and each carbonyl group supplies 2 electrons. Each metal atom supplies one electron to each other metal atom with a single bond, totalling three electrons. Since iron has eight d electrons, the total number of electrons is 18 for each atom.

The choice of ligand also affects the population of the electrons in the first triplet state of the core atoms, and, through this mechanism, affects the saturation level of the complex. The ligand provides a path for electron decay out of the first triplet state and provides a charge transfer state for transfer to the excited triplet state. However, the choice of ligand does not negate the RSA effect, and instead only modifies the saturation level of the complex.

Thus, ligands that satisfy the 18 electron rule for bonding the complex together also produce RSA behavior. The saturation value of the RSA behavior may be tuned with the choice of ligand, as well as the concentration of the RSA material in the carrier and the other factors discussed previously.

To verify the applicability of the previously stated principles, a number of organometallic cluster compounds with transition metal cores have been synthesized and tested, in addition to cyclopentadienyl iron carbonyl tetramer.

$HFeCo_3(CO)_{12}$ (mu-hydride-iron tricobalt dodecacarbonyl) was prepared by the method disclosed by Chini et al., Gazetta, vol. 90 (1960), pages 1005-1020. Twenty-nine-point-six (29.6) grams of $Co_2(CO)_8$ and 10.3 grams of $Fe(CO)_5$ were added to a 500 milliliter three-necked flask under argon. Ninety-five milliliters of degassed acetone was added through a dropping funnel. The black solution was magnetically stirred and heated to 40° C. for 4 hours. The temperature was raised to 60° C. for 15 hours. The volatiles were removed under vacuum and the black solid was removed in the glove box to yield 39.8 grams of crude intermediate product $[Co(CH_3COCH_3)_6][FeCo_3(CO)_{12}]_2$. Twenty (20) grams of the crude intermediate product was added to 250 milliliters of argon-degassed water and stirred for 5 minutes. Two hundred milliliters (200) of concentrated hydrochloric acid which had been argon degassed was added and stirred for 15 minutes. The reddish-violet precipitate was filtered off using a coarse frit in air from the greenish filtrate. The precipitate was washed with about 50 milliliters of water and dried under vacuum. The precipitate was added to 210 milliliters of toluene, which was heated to boiling and filtered in a glove box. The filtrate was cooled and the crystals separated, yielding 10.6 grams of the final product.

$[NEt_4]FeCo_3(CO)_{12}$ (tetra ethyl ammonium iron tricobalt dodecacarbonyl) was prepared by dissolving 7.3 grams of the intermediate $[Co(CH_3COCH_3)_6][FeCo_3(CO)_{12}]_2$ of the prior synthesis in 100 milliliters of deionized water and filtered in air. Two-point-four (2.4) grams of tetraethyl ammonium bromide in 50 milliliters of water was added to the solution and the precipitate filtered and dried under vacuum. The dried precipitate was stored under argon.

$HFeCo_3(CO)_{10}(PMe_3)_2$ (mu-hydrido iron tricobalt decacarbonyl bistrimethyl phosphine) was prepared by mixing together 0.75 grams of $HFeCo_3(CO)_{12}$ with 0.3 milliliters of $(PMe_3)$ in a flask with 70 milliliters of toluene and boiled in a glove box for 1 hour, under argon in the absence of air. The solution was filtered hot and upon cooling 250 milligrams of black crystals were filtered off. The crystals were redissolved in toluene and recrystallized to purify them.

$HFeCo_3(CO)_{10}(P(C_6H_5)_3)_2$ (mu-hydrido iron tricobalt decacarbonyl bistriphenyl phosphine) was prepared as for the -trimethyl phosphine compound just discussed, except for substituting -triphenyl phosphine for the -trimethyl phosphine.

Other compounds of the family can also be prepared by known procedures. For example, the ruthenium analog of cyclopentadienyl iron carbonyl tetramer can be prepared by procedures known in the art, see T. Blackmore et al., "Chemistry of the Metal Carbonyls. Part LIII. Some Dicarbonyl-(pi-cyclopentadienyl) Ruthenium Complexes Containing Metal-Metal Bonds", J. Chem. Soc. (A) (1968) pages 2931-2936.

Figure 6:
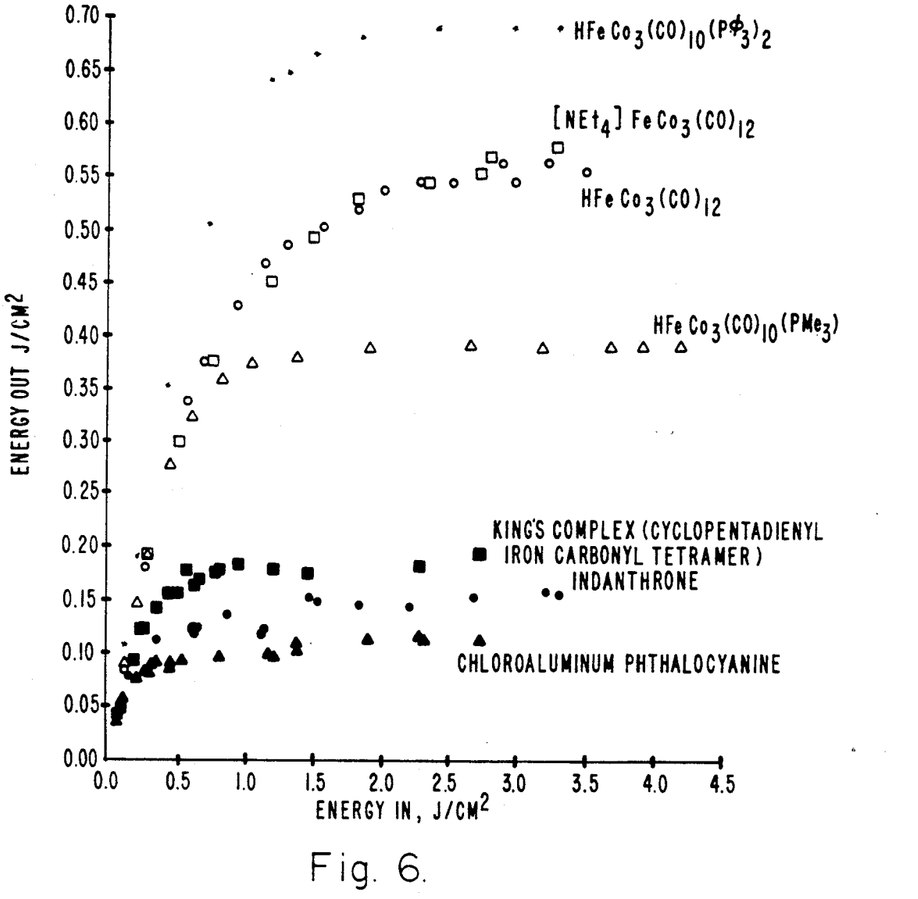
FIG. 6 is a graph of transmitted light as a function of incident light for some RSA absorber materials.

Test results for the preferred RSA material, the other materials prepared in the manner described above, and some prior art compounds not related to the present invention are presented in FIG. 6. To conduct these measurements, the organometallic cluster compound was dissolved to a concentration of about $5 \times 10^{-4}$ molar in methylene chloride solvent, while the other RSA materials were dissolved in effective solvents. A cell was prepared with a length parallel to the axis of measurement of 0.1-1.0 centimeter. The length of the cell was selected such that about 75 percent of the light was absorbed in the RSA material, but that length was small, about 0.1 centimeters for the compounds of the invention and chloroaluminum phthanocyanine, and large, about 1.0 centimeter, for Indanthrone. The intensity of transmitted light was measured as a function of the intensity of incident light at 532 nanometers wavelength was measured with a photocell, and the results depicted in FIG. 6.

In general, a low saturation level is desirable, as such a compound produces the greatest protection. As seen in FIG. 6, the preferred cyclopentadienyl iron carbonyl tetramer has a slightly higher saturation level than Indanthrone and chloroaluminum phthanocyanine, both prior art RSA materials. However, Indanthrone has the shortcoming that it has very low solubility in common solvents, and chloroaluminum phthanocyanine has a strong Soret band in the visible range, indicating that it is not effective over the entire visible spectrum. The other compounds in accordance with the invention are all operable, but produce even higher saturation levels.

The present invention provides an approach for protecting light sensitive devices with a new class of reverse saturable absorber materials that have greater industrial utility than prior materials. The transition metal cluster compounds of the invention also have the important advantage that they offer the opportunity to tailor the absorber material to specific applications, which is not readily done for prior RSA materials. The cluster compounds of the invention can be modified by changing the core metals and using mixtures of core metals, and by changing the ligands to affect the electronic transitions between triplet states. Coupled with their excellent solubility in carriers such as solvents and polymers, the cluster compounds of the invention, this ability to vary the properties permits the designer of particular protective materials wide ranging flexibility.

Although a particular embodiment of the invention has been described in detail for purposes of illustration, various modifications may be made without departing from the spirit and scope of the invention. Accordingly, the invention is not to be limited except as by the appended claims.

What is claimed is:

1. A passive optical protector comprising:

a shield for limiting the intensity of visible light passing through said shield, said shield comprising an absorber medium having reverse saturable absorption properties in the visible light spectrum, said absorber medium comprising an organometallic cluster compound selected from the group consisting of cyclopentadienyl iron carbonyl tetramer, cyclopentadienyl ruthenium carbonyl tetramer, mu-hydride-iron tricobalt dodecacarbonyl, tetra ethyl ammonium iron tricobalt dodecacarbonyl, mu-hydrido iron tricobalt decacarbonyl bis-trimethyl phosphine, and mu-hydrido iron tricobalt decacarbonyl bistriphenyl, wherein the absorber medium further comprises a carrier for the organometallic cluster compound and the carrier is a solid polymer.

* * * * *